United States Patent [19]

Williams, III

[11] 3,933,862

[45] Jan. 20, 1976

[54] AROMATIC DITHIO DIANHYDRIDES

[75] Inventor: Frank J. Williams, III, Scotia, N.Y.

[73] Assignee: General Electric Company, Schenectady, N.Y.

[22] Filed: Aug. 23, 1974

[21] Appl. No.: 500,136

[52] U.S. Cl. ....... 260/346.3; 260/326 S; 260/78 TF
[51] Int. Cl.² .................................... C07D 307/89
[58] Field of Search .............................. 260/346.3

[56] References Cited
FOREIGN PATENTS OR APPLICATIONS
2,155,431  8/1972  Germany Primary Examiner—Henry R. Jiles
Assistant Examiner—Bernard I. Dentz
Attorney, Agent, or Firm—William A. Teoli; Joseph T. Cohen; Jerome C. Squillaro

[57] ABSTRACT

There are provided bis(thioether) aromatic dianhydrides and method for making these materials. A bisthiol in the presence of base, or bisthiol basic salt, can be reacted with a nitro- or halo-substituted phthalic compound, such as an anhydride or anhydride precursor. These aromatic dithiodianhydrides can be used to make polyimides and polyesters, and can be used as curing agents for epoxy resins.

5 Claims, No Drawings

AROMATIC DITHIO DIANHYDRIDES

The present invention relates to the synthesis of aromatic dianhydrides useful as intermediates for making polyimides and to the bis(thioether) aromatic dianhydrides made thereby.

The bis(thioether) aromatic dianhydrides of the present invention, hereinafter referred to as the "dithiodianhydrides", are shown by the following formula, (I) 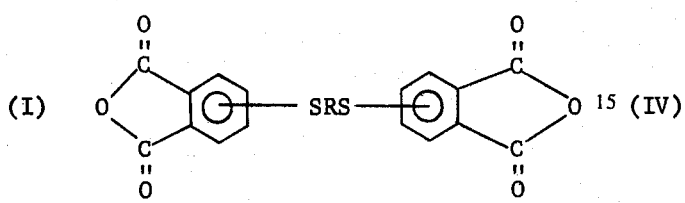

where R is a divalent aromatic radical having from 6-30 carbon atoms.

Included by the "dithiodianhydrides" of formula I are compounds of the formulas, (II) 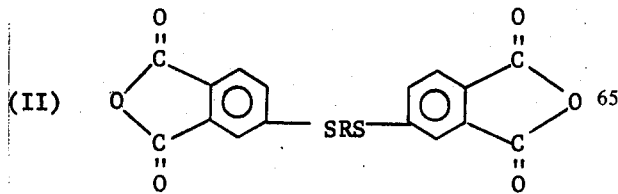

(III) 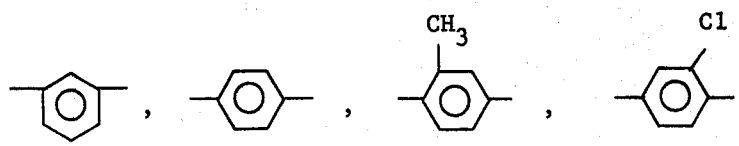

(IV) 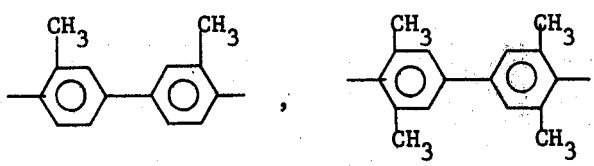

where R is as previously defined. Radicals included by R of formulas I-IV, for example

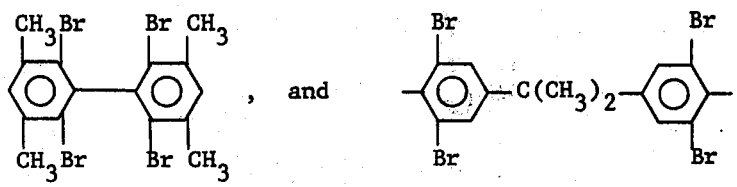

and (b) divalent organic radicals of the general formula

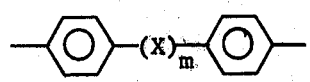

where X is a member selected from the class consisting of divalent radicals of the formulas, $-C_yH_{2y}-$,

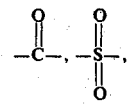

$-O-$, and $-S-$, where $m$ is 0 or 1, $y$ is a whole number from 1 to 5.

Included by the bis(thioether) dianhydrides of formula (II) are compounds such as 2,2-bis[4-(3,4-dicarboxythiophenoxy)phenyl] propane dianhydride, 2,4-bis[3,4-dicarboxyphenylthio]chlorobenzene dianhydride, 4,4'-bis[3,4-dicarboxyphenylthio] diphenylether dianhydride.

Dianhydrides included by formula (III) are for example 2,2-bis[4-(2,3-dicarboxythiophenoxy)phenyl] propane dianhydride, 2,4-bis[2,3-dicarboxyphenylthio] chlorobenzene dianhydride, 4,4'-bis[2,3-dicarboxyphenylthio] diphenylether dianhydride, 4,4'-bis[2,3-dicarboxyphenylthio] biphenyl dianhydride.

Dianhydrides included by formula (IV) are for example, 2-[4-(3,4-dicarboxythiophenoxy)phenyl] , 2-[4-(2,3-dicarboxythiophenoxy)phenyl] propane dianhydride and 4,4'-[2,3-dicarboxyphenylthio] [3,4-dicarboxyphenylthio] diphenylether dianhydride.

One procedure for making dithiodianhydrides of formulas I–IV is by effecting reaction in the presence of base between an aromatic dithiol of the formula, (V)  HSRSH, and a substituted anhydride of the formula

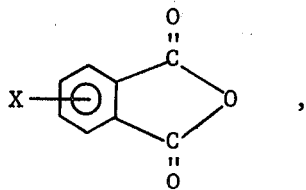

(VI)

where R is as previously defined, and X is a radical selected from nitro, chloro, fluoro, bromo, etc.

Another procedure which can be used to make the thiodianhydrides of formulas I–IV is by effecting reaction in the presence of base between aromatic dithiol of formula (V) and substituted phthalimides of the formula,

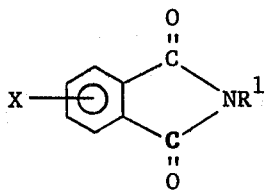

(VII)

to produce an intermediate bisimide of the formula,

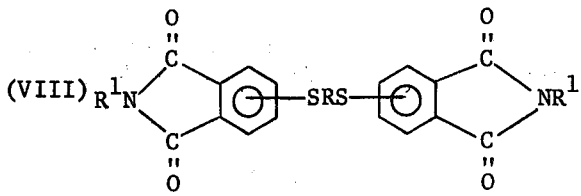

(VIII)

which is hydrolyzed with base to produce the corresponding tetra acid salt followed by acidification and dehydration of the tetra acid to the dithiodianhydride, where $R^1$ is a monovalent organo radical selected from the class consisting of $C_{(1-8)}$ alkyl radicals, and organic radicals having from 6–20 carbon atoms, selected from the class consisting of aromatic hydrocarbon radicals and halogenated derivatives thereof. Alternatively, a preformed basic salt of the aromatic dithiol of formula (V), such as (IX)  MSRSM, where R is as previously defined and M is an alkali metal, such as sodium, potassium, lithium, etc., can be reacted with compounds of formulas VI–VII to produce respectively the dithiodianhydride of formulas I–IV, or the bisimide of formula VIII.

Included by the bisimides of formula (VIII) are for example, 4,4'-bis(N-phenylphthalimide-3-thio)diphenyl-2,2-propane; 4,4'-bis(N-phenylphthalimide-4-thio)diphenyl-2,2-propane; 4,4'-bis(N-methylphthalimide-3-thio)diphenylether; 4,4'-bis(N-phenylphthalimide-4-thio)biphenyl; 4,4'-(N-phenylphthalimide-3-thio)(N-phenylphthalimide-4-thio)diphenylether, etc. These bisimides can be used as plasticizer for polyvinyl chloride, polyimides and as anti-oxidizing agents.

Additional procedures which can be used to make the aromatic dithiodianhydrides of the present invention are by using the corresponding tetra nitriles and tetra esters as source materials as shown in Heath et al U.S. Pat. No. 3,787,475 assigned to the same assignee as the present invention.

Radicals included by $R^1$ are, for example, phenyl, tolyl, xylyl, naphthyl, chlorophenyl, bromonaphthyl, etc., and alkyl radicals such as methyl, ethyl, etc.

Aromatic dithiol included by formula V as for example, 4-chlorobenzenedithiol, 4,4'-diphenyletherdithiol, 4,4'-diphenyldithiol, 2,2-bis(4-mercaptophenyl)propane, m-benzenedithiol, etc.

One method of preparing the dithiodianhydrides of the present invention as described above is by effecting reaction between the aromatic dithiol and a substituted anhydride in the presence of base. Included by the bases which can be used are alkali metal carbonates, for example sodium carbonate, potassium carbonate, lithium carbonate, etc. and various organic amines such as tertiary amines for example, triethylamine, pyridine, 1,4-diazobicyclo-[2.2.2]octane (DABCO), 1,5-diazobicyclo[4.3.0]nonene-5(DBN).

There can be utilized a dipolar aprotic organic solvent such as dimethylformamide, dimethylacetamide, N-methyl-2-pyrrolidone, etc.

Another procedure which can be used to make the thiodianhydrides of the present invention is by using a substituted phthalimide of the formula VII as described to produce an intermediate bisimide of Formula (VIII) employing a preformed basic salt of the aromatic dithiol. Anhydrous conditions can be used along with a dipolar aprotic solvent as described above employing temperatures in the range of from 25°C. to 150°C.

The thiodianhydride of the present invention can be employed to make polythioetherimides as shown in copending application Ser. No. 500,137 filed concurrently herewith by reacting such thiodianhydrides with organic diamines under either melt polymerization conditions or by effecting reaction between such ingredients in the presence of an inert non-polar organic solvent. The thiodianhydride of the present invention also can be used as curing agents for epoxy resins. In addition the thiodianhydrides can be employed to make a variety of polyesters and polyesteramides.

In order that those skilled in the art will be better able to practice the invention the following examples are given by way of illustration and not by way of limitation. All parts are by weight.

EXAMPLE 1

A mixture of 1.40 part of 3-chlorophthalic anhydride, one part of 2,2-bis(4-mercaptophenol)propane and 9.4 parts of anhydrous dimethylformamide were stirred at room temperature under a nitrogen atmosphere. There was added to the mixture while it was stirred 0.89 part of triethylamine and resulting red solution was stirred at 40°C. for 2 hours. The resulting yellow mixture was then cooled to room temperature and added slowly to 200 parts of 1.2 HCl. There was obtained a yellow precipitate which was collected by filtration and then dried to give 2.1 parts of a crude product. The crude product was treated with a mixture of acetic acid and acetic anhydride. Recrystallization of this product from a toluene acetic anhydride mixture resulted in the production of a product having a melting point of 211.5°–213°C. Based on method of preparation the product was a thiodianhydride of the formula

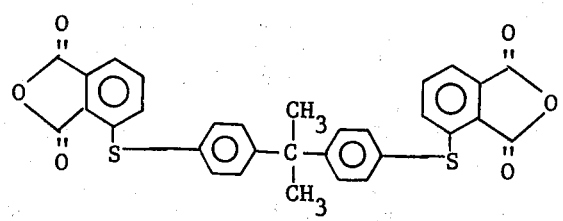

The identity of the product was confirmed by its infrared spectrum and mass spectral and $^{13}$C NMR analysis.

EXAMPLE 2

The procedure of Example 1 was repeated except that there was employed 1.2 parts of 3-fluorophthalic anhydride per one part of the 2,2-bis(4-mercaptophenyl)propane. The resulting reaction mixture was poured into 200 parts of 1.2 NHCl and there was obtained a 99% yield of a yellow precipitate. The crude product was then treated with a mixture of acetic acid/acetic anhydride to produce an 80% yield of a product having a melting point of 208°–210°C. Recrystallization of the crude product from a toluene/acetic acid anhydride mixture resulted in the production of a product having a melting point of 211.5°–213°C. which was identical to the thiodianhydride made in Example 1.

EXAMPLE 3

A mixture of 6.2 parts of 3-chlorophthalic anhydride, 3 parts of 4-chloro-m-benzenedithiol, and 28 parts of anhydrous dimethylformamide was stirred at room temperature under a nitrogen atmosphere. There was added to the resulting mixture, 3.9 parts of triethylamine. The resulting solution was stirred for 16 hours at room temperature. The mixture was then added to 100 parts of 1.2 N/HCl. There was obtained a precipitate which was collected and dried. The product was treated with acetic acid/acetic anhydride mixture to give a yellow crystalline dianhydride having a melting point of 163.5°–166.5°C. The yield of final product was approximately 60%. Based on the method of preparation and its infra-red and mass spectral analysis as well as $^{13}$C NMR analysis the product was

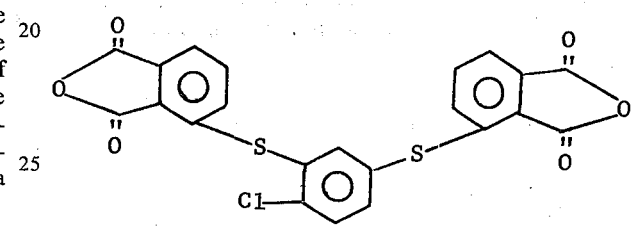

EXAMPLE 4

A mixture of 2.9 parts of the disodium salt of 2,2-bis(4-mercaptophenyl)propane and 5.1 parts of 3-nitro-N-phenyl phthalimide was stirred with 36 parts of anhydrous dimethylformamide under a nitrogen atmosphere. The mixture was stirred at room temperature for 2 hours and added to 500 parts of methanol. The resulting precipitate was collected and dried to give 5.1 parts of a yellow powder having a melting point of 148°–150°C. Based on method of preparation as well as infra-red and mass spectral and $^{13}$C NMR analysis the product was a bisimide of the formula

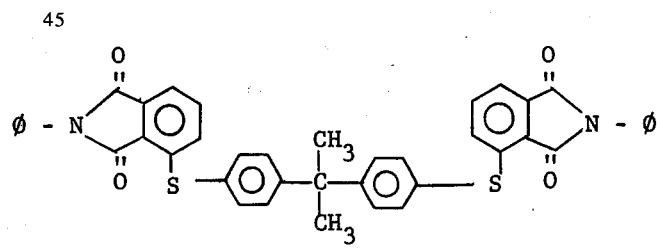

EXAMPLE 5

The procedure of Example 4 was repeated except that in place of the 3-nitro-N-phenylphthalimide there was substituted 4-nitro-N-phenylphthalimide to produce a mixture of 3.5 parts of a disodium salt, 6.15 parts of the phthalimide and 55 parts of the dimethylformamide. The mixture was heated at 60°C. for 4 hours and allowed to cool to room temperature. It was then added to 400 parts of methanol. There was obtained 5.94 parts of a precipitate. Based on method of preparation and its infra-red and mass spectral analysis, the product was a bisimide of the formula,

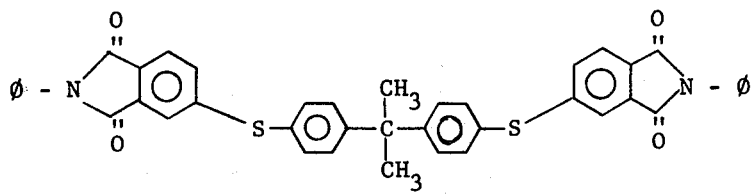

One part of this bisimide was treated with one part of 50% aqueous sodium hydroxide and 2 parts of water at reflux. The resulting homogeneous solution was acidified and the tetraacid shown below was collected by filtration

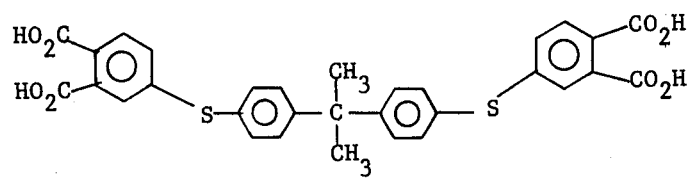

This material was treated with a 20% excess of acetic anhydride in refluxing acetic acid to give in good yield a thioetherdianhydride of the structure shown

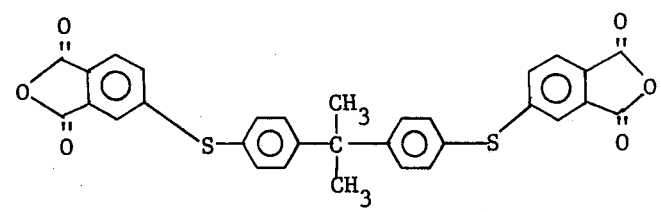

The identity of the product was confirmed by infrared, 1H and $^{13}$C NMR analysis.

EXAMPLE 6

The procedure of Example 1 was repeated except that there was employed 3.0 parts of 4,4'-diphenyletherdithiol, 4.68 parts of 3-chlorophthalic anhydride, 2.85 parts of triethylamine and 38 parts of anhydrous DMF. The mixture was stirred at 50°C. for 3 hours to give a product which after acetic acid/acetic anhydride treatment consisted of a 93% yield of product. Recrystallization of this material from toluene/acetic anhydride gave a product in 87% yield, mp 224°–228°C. Based on the method of preparation the product was a thioetherdianhydride of the formula

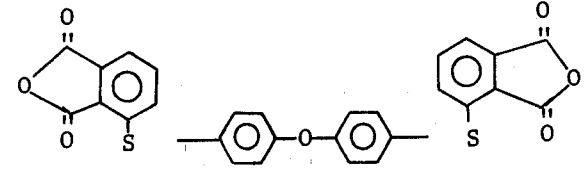

The identity of the product was confirmed by elemental and mass spectral analyses. Calcd. for $C_{28}H_{14}O_6S_2$; C, 63.9; H, 2.7; Found: C, 64.1; H, 2.9.

EXAMPLE 7

The procedure of Example 6 was repeated except that there was employed 3.0 parts of 4,4'-diphenylether dithiol, 4.68 parts of 4-chlorophthalic anhydride, 2.85 parts of triethylamine and 38 parts of anhydrous DMF. After workup and recrystallization from toluene/acetic anhydride a 91% yield of product mp 186.5°–188.5°C. was obtained. Based on the method of preparation and mass spectral analysis the product was a thioetherdianhydride of the formula

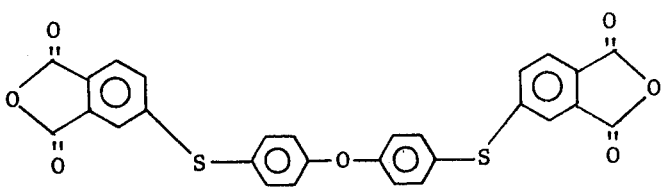

EXAMPLE 8

The procedure of Example 6 was repeated using 3.0 parts of 4,4'-diphenyletherdithiol, 3.28 parts of 3-nitrophthalic anhydride, 2.85 parts of triethylamine, and 31 ml of anhydrous DMF. The mixture was worked up as described previously to give a product which after recrystallization was isolated in 38% yield, mp 207°–218°C. The structure was identical to that obtained in Example 6.

EXAMPLE 9

The procedure of Example 1 was repeated using 2.50 parts of 4,4'-diphenyldithiol, 4.18 parts of 3-chlorophthalic anhydride, 2.56 parts of triethylamine, and 34 parts of anhydrous DMF. After workup and recrystallization a 73% yield of product 307.5°–308.5°C. was obtained. Based on the method of preparation the product was a thioetherdianhydride of the formula

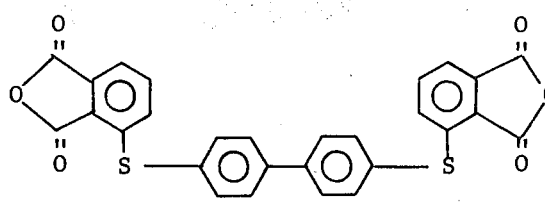

The identity of the compound was confirmed by infrared and mass spectral analysis and by elemental analysis: Calcd. for $C_{28}H_{14}O_6S_2$; C, 65.9; H, 2.7; Found: C, 64.5; H, 3.7.

EXAMPLE 10

The procedure of Example 9 was repeated except that 2.50 parts of 4,4-diphenyldithiol, 4.18 parts of 4-chlorophthalic anhydride, 2.56 parts of triethylamine, and 34 parts of anhydrous DMF were used. After workup and recrystallization a 58% yield of product, mp 240.0°–241.5°C. was obtained. Based on the method of preparation the product was a thioetherdianhydride of the formula The identity of the product was confirmed by infra-red and mass spectral analysis and by elemental analysis: Calcd. for $C_{28}H_{14}O_6S_2$; C, 65.9; H, 2.8; Found: C, 66.3; H, 3.1.

EXAMPLE 11

The procedure of Example 6 was repeated except that 1.50 parts of 4,4-diphenyletherdithiol, 1.64 parts of 3-fluorophthalic anhydride, 1.46 parts of triethylamine and 15 parts of anhydrous DMF were used. After workup and recrystallization a 42% yield of product, mp 235.0°–237.5°C. was obtained. Based on the method of preparation and infra-red and mass spectral analysis the product was a thioether dianhydride of the formula

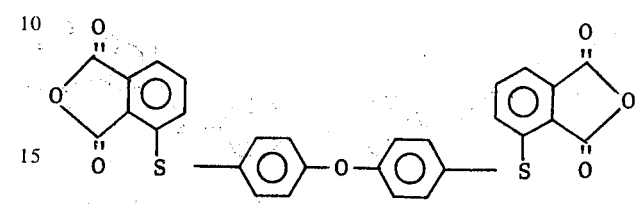

EXAMPLE 12

A mixture of 3.00 parts of 4,4'-diphenyletherdithiol, 6.87 parts of 3-nitro-N-phenylphthalimide, 2.84 parts of triethylamine and 50 parts of anhydrous DMF was stirred at 50°C. under a nitrogen atmosphere for 3 hours. The solution was cooled to room temperature and poured into 200 parts of 1.2 N/HCl solution. The resulting precipitate was collected by filtration and dried. This crude product was stirred with methanol (1 part of bisimide to 4 parts of methanol) at reflux and filtered to give a 93% yield of product, mp 227°–229°C. Based on its infra-red and $^{13}C$ spectra as well as the method of preparation the product was a bisimide of the structure

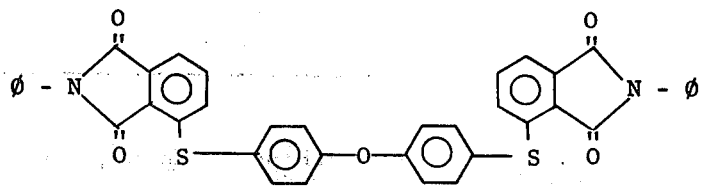

EXAMPLE 13

A mixture of 3 parts of 4,4'-diphenyletherdithiol, 6.87 parts of 4-nitro-N-phenylphthalimide, 2.84 parts of triethylamine, and 50 parts of anhydrous DMF was stirred at 50°C. under a nitrogen atmosphere for 3 hours. The mixture was cooled to room temperature and poured into 200 ml of 1.2 N HCl. The resulting precipitate was collected by filtration and dried. The crude product was stirred with methanol (1 part of bisimide to 4 parts of methanol) at reflux and after cooling the solution was filtered to give a 97% yield of product, mp 261°–265°C. Based on its infra-red and $^{13}C$ spectra as well as the method of preparation the product was a bisimide of the structure

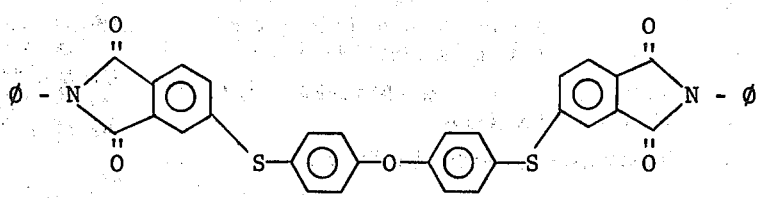

One part of this bisimide was treated with 1 parts of 50% aqueous sodium hydroxide and 2 parts of water at reflux. The resulting homogeneous solution was acidified and the tetraacid shown below was collected by filtration.

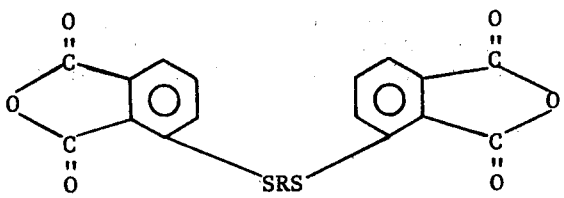

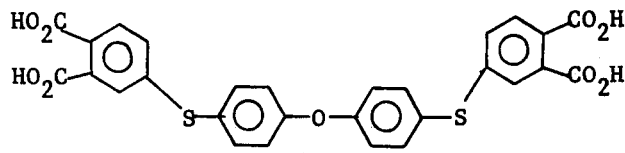

This material was treated with a 20% excess of acetic anhydride in refluxing acetic acid to give in good yield a thioetherdianhydride identical to that obtained in Example 7.

The thiodianhydride of the present invention can be employed as epoxy curing catalysts. For example, a mixture of 65 parts of the thiodianhydride of Example 1 is mixed with 100 parts of an epoxy resin in the form of a reaction product of 4,4'-isopropylidenediphenol and epichlorohydran. It is found that after the mixture is heated at 200°C that complete cure of epoxy resin results after 24 hours.

Although the above examples are limited to only a few of the very many thiodianhydrides which can be made in the practice of the invention it should be understood that a much broader class of thiodianhydrides such as shown by formula 1 can be made. A variety of procedures are shown in the description preceding these examples for making such thiodianhydrides.

What I claim as new and desire to secure by Letters Patent of the United States is:

1. A dithioanhydride having the formula where R is a radical selected from the class consisting of

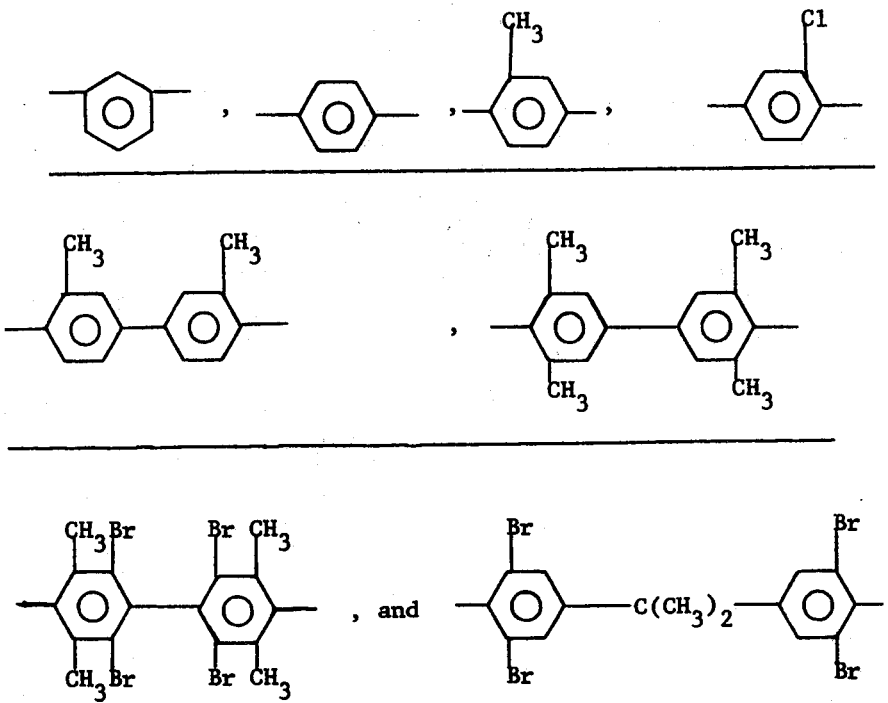

and divalent organic radicals of the general formula

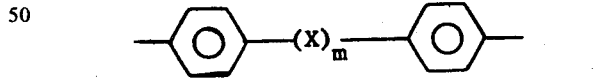

where X is a member selected from the class consisting of divalent radicals of the formulas, $-C_yH_{2y}-$,

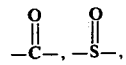

$-O-$, and $-S-$, where $m$ is 0 or 1, $y$ is a whole number from 1 to 5.

2. The compound 2,2-bis[4-(2,3-dicarboxythiophenoxy)phenyl]propane dianhydride.

3. The compound 2,4-bis[2,3-dicarboxyphenylthio]-chlorobenzene dianhydride.

4. The compound 4,4'-bis[2,3-dicarboxyphenylthio] diphenylether dianhydride.

5. The compound 4,4'-bis[2,3-dicarboxyphenylthio] biphenyl dianhydride.

* * * * *